(12) United States Patent
Fisher

(10) Patent No.: US 8,575,462 B2
(45) Date of Patent: Nov. 5, 2013

(54) SWEET CORN LINE SYW-6R07086

(75) Inventor: David Elon Fisher, Waunakee, WI (US)

(73) Assignee: Seminis Vegetable Seeds, Inc., Woodland, CA (US)

( * ) Notice: Subject to any disclaimer, the term of this patent is extended or adjusted under 35 U.S.C. 154(b) by 0 days.

(21) Appl. No.: 13/346,516

(22) Filed: Jan. 9, 2012

(65) Prior Publication Data

US 2013/0180003 A1 Jul. 11, 2013

(51) Int. Cl.
- *A01H 5/10* (2006.01)
- *A01H 5/00* (2006.01)
- *A01H 4/00* (2006.01)
- *A01H 1/02* (2006.01)
- *C12N 15/82* (2006.01)
- *C12N 5/10* (2006.01)
- *A23J 3/14* (2006.01)

(52) U.S. Cl.
USPC ..... 800/320.1; 800/275; 800/278; 800/300.1; 435/412; 435/424; 435/430; 426/655

(58) Field of Classification Search
None
See application file for complete search history.

(56) References Cited

U.S. PATENT DOCUMENTS 7,193,144 B2 * 3/2007 Grote .................. 800/320.1

OTHER PUBLICATIONS

Moose SP, Mumm RH., "Molecular plant breeding as the foundation for 21st century crop improvement", *Plant Physiol.*; 147(3):969-77; Jul. 2008.
Variety specific information as indicated in transmittal letter of Apr. 22, 2013 Information Disclosure Statement for U.S. Appl. No. 13/346,516.
Hu, G. and S. H. Hulbert; "Construction of 'compound' rust genes in maize," *Euphytica*; 87: 45-51; 1996.

* cited by examiner

*Primary Examiner* — David T Fox
*Assistant Examiner* — Steven Bernacki
(74) *Attorney, Agent, or Firm* — Dentons US LLP; Alissa Eagle Esq.

(57) ABSTRACT

The invention provides seed and plants of the sweet corn line designated SYW-6R07086. The invention thus relates to the plants, seeds and tissue cultures of sweet corn line SYW-6R07086, and to methods for producing a sweet corn plant produced by crossing a plant of sweet corn line SYW-6R07086 with itself or with another sweet corn plant, such as a plant of another line. The invention further relates to seeds and plants produced by such crossing. The invention further relates to parts of a plant of sweet corn line SYW-6R07086, including the seed, pod, and gametes of such plants.

22 Claims, No Drawings

SWEET CORN LINE SYW-6R07086

FIELD OF THE INVENTION

The present invention relates to the field of plant breeding and, more specifically, to the development of sweet corn line SYW-6R07086.

BACKGROUND OF THE INVENTION

The goal of vegetable breeding is to combine various desirable traits in a single variety/hybrid. Such desirable traits may include any trait deemed beneficial by a grower and/or consumer, including greater yield, better stalks, better roots, resistance to insecticides, herbicides, pests, and disease, tolerance to heat and drought, reduced time to crop maturity, better agronomic quality, higher nutritional value, sugar content, uniformity in germination times, stand establishment, growth rate and maturity, among others.

Breeding techniques take advantage of a plant's method of pollination. There are two general methods of pollination: a plant self-pollinates if pollen from one flower is transferred to the same or another flower of the same plant or plant variety. A plant cross-pollinates if pollen comes to it from a flower of a different plant variety.

Plants that have been self-pollinated and selected for type over many generations become homozygous at almost all gene loci and produce a uniform population of true breeding progeny, a homozygous plant. A cross between two such homozygous plants of different genotypes produces a uniform population of hybrid plants that are heterozygous for many gene loci. Conversely, a cross of two plants each heterozygous at a number of loci produces a population of hybrid plants that differ genetically and are not uniform. The resulting non-uniformity makes performance unpredictable.

The development of uniform varieties requires the development of homozygous inbred plants, the crossing of these inbred plants, and the evaluation of the crosses. Pedigree breeding and recurrent selection are examples of breeding methods that have been used to develop inbred plants from breeding populations. Those breeding methods combine the genetic backgrounds from two or more plants or various other broad-based sources into breeding pools from which new lines are developed by selfing and selection of desired phenotypes. The new lines are evaluated to determine which of those have commercial potential.

SUMMARY OF THE INVENTION

In one aspect, the present invention provides a sweet corn plant of the line designated SYW-6R07086. Also provided are corn plants having all the physiological and morphological characteristics of such a plant. Parts of these corn plants are also provided, for example, including pollen, an ovule, and a cell of the plant.

In another aspect of the invention, a plant of sweet corn line SYW-6R07086 comprising an added heritable trait is provided. The heritable trait may comprise a genetic locus that is, for example, a dominant or recessive allele. In one embodiment of the invention, a plant of sweet corn line SYW-6R07086 is defined as comprising a single locus conversion. In specific embodiments of the invention, an added genetic locus confers one or more traits such as, for example, male sterility, herbicide resistance, insect resistance, resistance to bacterial, fungal, sugar content, nematode or viral disease, and altered fatty acid, phytate or carbohydrate metabolism. In further embodiments, the trait may be conferred by a naturally occurring gene introduced into the genome of a line by backcrossing, a natural or induced mutation, or a transgene introduced through genetic transformation techniques into the plant or a progenitor of any previous generation thereof. When introduced through transformation, a genetic locus may comprise one or more genes integrated at a single chromosomal location.

The invention also concerns the seed of sweet corn line SYW-6R07086. The corn seed of the invention may be provided as an essentially homogeneous population of corn seed of the line designated SYW-6R07086. Essentially homogeneous populations of seed are generally free from substantial numbers of other seed. Therefore, seed of line SYW-6R07086 may, in particular embodiments of the invention, be defined as forming at least about 97% of the total seed, including at least about 98%, 99% or more of the seed. The population of sweet corn seed may be particularly defined as being essentially free from hybrid seed. The seed population may be separately grown to provide an essentially homogeneous population of sweet corn plants designated SYW-6R07086.

In yet another aspect of the invention, a tissue culture of regenerable cells of a sweet corn plant of line SYW-6R07086 is provided. The tissue culture will preferably be capable of regenerating corn plants capable of expressing all of the physiological and morphological characteristics of the starting plant, and of regenerating plants having substantially the same genotype as the starting plant. Examples of some of the physiological and morphological characteristics of the line SYW-6R07086 include those traits set forth in the tables herein. The regenerable cells in such tissue cultures may be derived, for example, from embryos, meristematic cells, immature tassels, microspores, pollen, leaves, anthers, roots, root tips, silk, kernels, ears, cobs, husks, or stalks, or from callus or protoplasts derived from those tissues. Still further, the present invention provides corn plants regenerated from a tissue culture of the invention, the plants having all the physiological and morphological characteristics of line SYW-6R07086.

In still yet another aspect of the invention, processes are provided for producing corn seeds, plants and parts thereof, which processes generally comprise crossing a first parent sweet corn plant with a second parent corn plant, wherein at least one of the first or second parent corn plants is a plant of the line designated SYW-6R07086. These processes may be further exemplified as processes for preparing hybrid corn seed or plants, wherein a first corn plant is crossed with a second corn plant of a different, distinct genotype to provide a hybrid that has, as one of its parents, the sweet corn plant line SYW-6R07086. In these processes, crossing will result in the production of seed. The seed production occurs regardless of whether the seed is collected or not.

In one embodiment of the invention, the first step in "crossing" comprises planting seeds of a first and second parent corn plant, often in proximity so that pollination will occur for example, naturally or manually. Where the plant is self-pollinated, pollination may occur without the need for direct human intervention other than plant cultivation. For hybrid crosses, it may be beneficial to detassel or otherwise emasculate the parent used as a female.

A second step may comprise cultivating or growing the seeds of first and second parent corn plants into mature plants. A third step may comprise preventing self-pollination of the plants, such as by detasseling or other means.

A fourth step for a hybrid cross may comprise cross-pollination between the first and second parent corn plants. Yet another step comprises harvesting the seeds from at least one of the parent corn plants. The harvested seed can be grown to produce a corn plant or hybrid corn plant.

The present invention also provides the corn seeds and plants produced by a process that comprises crossing a first parent corn plant with a second parent corn plant, wherein at least one of the first or second parent corn plants is a plant of the line designated SYW-6R07086. In one embodiment of the invention, corn seed and plants produced by the process are first generation ($F_1$) hybrid corn seed and plants produced by crossing a plant in accordance with the invention with another, distinct plant. The present invention further contemplates plant parts of such an $F_1$ hybrid corn plant, and methods of use thereof. Therefore, certain exemplary embodiments of the invention provide an $F_1$ hybrid corn plant and seed thereof.

In still yet another aspect, the present invention provides a method of producing a plant derived from line SYW-6R07086, the method comprising the steps of: (a) preparing a progeny plant derived from line SYW-6R07086, wherein said preparing comprises crossing a plant of the line SYW-6R07086 with a second plant; and (b) crossing the progeny plant with itself or a second plant to produce a seed of a progeny plant of a subsequent generation. In further embodiments, the method may additionally comprise: (c) growing a progeny plant of a subsequent generation from said seed of a progeny plant of a subsequent generation and crossing the progeny plant of a subsequent generation with itself or a second plant; and repeating the steps for an additional 3-10 generations to produce a plant derived from line SYW-6R07086. The plant derived from line SYW-6R07086 may be an inbred line, and the aforementioned repeated crossing steps may be defined as comprising sufficient inbreeding to produce the inbred line. In the method, it may be desirable to select particular plants resulting from step (c) for continued crossing according to steps (b) and (c). By selecting plants having one or more desirable traits, a plant derived from line SYW-6R07086 is obtained which possesses some of the desirable traits of the line as well as potentially other selected traits.

In certain embodiments, the present invention provides a method of producing food or feed comprising: (a) obtaining a plant of corn line SYW-6R07086, wherein the plant has been cultivated to maturity, and (b) collecting at least one corn from the plant.

In still yet another aspect of the invention, the genetic complement of sweet corn plant line designated SYW-6R07086 is provided. The phrase "genetic complement" is used to refer to the aggregate of nucleotide sequences, the expression of which sequences defines the phenotype of, in the present case, a sweet corn plant, or a cell or tissue of that plant. A genetic complement thus represents the genetic makeup of a cell, tissue or plant, and a hybrid genetic complement represents the genetic make up of a hybrid cell, tissue or plant. The invention thus provides corn plant cells that have a genetic complement in accordance with the corn plant cells disclosed herein, and seeds and plants containing such cells.

Plant genetic complements may be assessed by genetic marker profiles, and by the expression of phenotypic traits that are characteristic of the expression of the genetic complement, e.g., isozyme typing profiles. It is understood that line SYW-6R07086 could be identified by any of the many well known techniques such as, for example, Simple Sequence Length Polymorphisms (SSLPs) (Williams et al., *Nucleic Acids Res.*, 1 8:6531 6535, 1990), Randomly Amplified Polymorphic DNAs (RAPDs), DNA Amplification Fingerprinting (DAF), Sequence Characterized Amplified Regions (SCARs), Arbitrary Primed Polymerase Chain Reaction (AP-PCR), Amplified Fragment Length Polymorphisms (AFLPs) (EP 534 858, specifically incorporated herein by reference in its entirety), and Single Nucleotide Polymorphisms (SNPs) (Wang et al., *Science*, 280:1077-1082, 1998).

In still yet another aspect, the present invention provides hybrid genetic complements, as represented by corn plant cells, tissues, plants, and seeds, formed by the combination of a haploid genetic complement of a corn plant of the invention with a haploid genetic complement of a second corn plant, preferably, another, distinct corn plant. In another aspect, the present invention provides a corn plant regenerated from a tissue culture that comprises a hybrid genetic complement of this invention.

In still yet another aspect, the invention provides a method of determining the genotype of a plant of sweet corn line SYW-6R07086 comprising detecting in the genome of the plant at least a first polymorphism. The method may, in certain embodiments, comprise detecting a plurality of polymorphisms in the genome of the plant. The method may further comprise storing the results of the step of detecting the plurality of polymorphisms on a computer readable medium. The invention further provides a computer readable medium produced by such a method.

Any embodiment discussed herein with respect to one aspect of the invention applies to other aspects of the invention as well, unless specifically noted.

The term "about" is used to indicate that a value includes the standard deviation of the mean for the device or method being employed to determine the value. The use of the term "or" in the claims is used to mean "and/or" unless explicitly indicated to refer to alternatives only or the alternatives are mutually exclusive. When used in conjunction with the word "comprising" or other open language in the claims, the words "a" and "an" denote "one or more," unless specifically noted otherwise. The terms "comprise," "have" and "include" are open-ended linking verbs. Any forms or tenses of one or more of these verbs, such as "comprises," "comprising," "has," "having," "includes" and "including," are also open-ended. For example, any method that "comprises," "has" or "includes" one or more steps is not limited to possessing only those one or more steps and also covers other unlisted steps. Similarly, any plant that "comprises," "has" or "includes" one or more traits is not limited to possessing only those one or more traits and covers other unlisted traits.

Other objects, features and advantages of the present invention will become apparent from the following detailed description. It should be understood, however, that the detailed description and any specific examples provided, while indicating specific embodiments of the invention, are given by way of illustration only, since various changes and modifications within the spirit and scope of the invention will become apparent to those skilled in the art from this detailed description.

DETAILED DESCRIPTION OF THE INVENTION

The invention provides methods and compositions relating to plants, seeds and derivatives of sweet corn line SYW-6R07086. This line shows uniformity and stability within the limits of environmental influence for the traits described hereinafter. Sweet corn line SYW-6R07086 provides sufficient seed yield. By crossing with a distinct second plant, uniform F1 hybrid progeny can be obtained. The development of sweet corn line SYW-6R07086 can be summarized as follows.

A. ORIGIN AND BREEDING HISTORY OF SWEET CORN LINE SYW-6R07086

SYY-6R07086 is a white sweet corn inbred which is homozygous both for the su1 gene and for the sh2 gene. The line was selected for bright white color. The development of parent line SYW-6R07086 can be summarized as follows:

Winter Year 1-2: The inbred line SYY093-678 (a proprietary Seminis inbred) was grown in the Seminis Melipilla, Chile nursery in row 8564 and was cross pollinated by inbred SHW084-SHSMHG9W (a proprietary Seminis inbred) grown in row 5387 to make an F1. This hybrid was designated SVR08727258 and given a source of E02: 8564 X 5387.

Winter Year 2-3: The hybrid SVR08727258 from source E02: 8564 X 5387 was grown in the Seminis Melipilla, Chile nursery in row 9214 and plants in that row were cross pollinated by inbred SYY093-678 (a proprietary Seminis inbred) grown in row 9206 to make a BC1. Ears harvested from this cross were given a source of E03: 9214 X 9205/B1.

Summer Year 3: The BC1 to inbred SYY093-678 from source E03: 9214 X 9205/B1 was grown in Seminis DeForest, Wis. nursery in row 5495 and self pollinated to give BC1F2 ears. N03: 5495/1. was the source designation given to one of the harvested ears.

Winter Year 3-4: White kernels from the BC1F2 seed from source N03: 5495/1. were selected and grown in Seminis Melipilla, Chile nursery row 5783 and self pollinated to make the BC1F3. E04: 5783/1. was the source designation given to one of the harvested ears. All kernels on this ear were a bright white.

Summer Year 4: The BC1F3 from source E04: 5783/1. was grown in Seminis DeForest, Wis. nursery in row 4492 and self pollinated to give BC1F4 ears. N04: 4492/1. was the source designation given to one of the harvested ears.

Winter Year 4-5: The BC1F4 from source N04: 4492/1. was grown in Seminis Melipilla, Chile nursery row 8812 and self pollinated to make the BC1F5. E05: 8812/2. was the source designation given to one of the harvested ears.

Summer Year 5: The BC1F5 from source E05: 8812/2. was grown in Seminis DeForest, Wis. nursery in row 5370 and self pollinated to give BC1F6 ears. N05: 5370/1. was the source designation given to one of the harvested ears.

Winter Year 5-6: The BC1F6 from source N05: 5370/1. was grown in Seminis Melipilla, Chile nursery row 5442 and was cross pollinated by inbred SYY093-678 (a proprietary Seminis inbred) grown in row 5441. 05 10 6R 6R MSME-E2__00021__00029__2_/was the source given to one of the harvested ears of this F1 cross.

Summer Year 6: The F1 from source 10 6R 6R MSME-E2__00021__00029__2_/was grown in Seminis DeForest, Wis. nursery in row 4474 and was cross pollinated by inbred SYY093-678 (a proprietary Seminis inbred) grown in row 4473 to make the BC1. 06 04 6R 6R WIDE-IB5__00009__00026__1>was the source given to one of the harvested ears from this cross.

Winter Year 6-7: The BC1 from source 06 04 6R, 6R WIDE-IB5__00009__00026__1> was grown in Seminis Melipilla, Chile nursery row 14054 and self pollinated to make the BC1F2 generation. 06 10 6R, 6R MSME-E2__00009__00080__7_. was the source given to one of the selfed ears harvested which was segregating for white and yellow kernels.

Summer Year 7: White kernels from the BC1F2 seed from source 06 10 6R, 6R MSME-E2__00009__00080__7_. were selected and grown in Seminis DeForest, Wis. nursery row 5783 and self pollinated to make the BC1F3. 07 04 6R, 6R WIDE-IB1__00008__00038__1_. was the source designation given to one of the harvested ears. This BC1F3 was given the name SYY-6R07086.

Winter Year 7-8: The BC1F3 of SYY-6R07086 from source 07 04 6R, 6R WIDE-IB1__00008__00038__1_. was grown in Seminis Melipilla, Chile nursery row 18744 and self pollinated to make the BC1F4 generation. 07 10 6R, 6R MSME-E2__00016__00007_@_. was the source given to a bulk of the selfed ears harvested.

Summer Year 9: The BC1F4 of SYY-6R07086 from source 07 10 6R, 6R MSME-E2__00016__00007_@_. was sent to Foundation Seed for increase.

Corn inbred SYW-6R07086 was named at the BC1F3 generation. This inbred was reproduced by self pollination in the winter of year 12-13 in Melipilla, Chile winter nursery and judged to be stable. A bulk of ears BC1F4 ears from that nursery was sent to Foundation Seed as Breeder's Seed.

Inbred SYW-6R07086 is uniform for the traits observed. SYW-6R07086 shows no variants other than what would normally be expected due to environment or that would occur for almost any character during the course of repeated sexual reproduction. SYW-6R07086 resembles inbred lines SYY093-678, SYY-6R07001 and SYY-6R07003 although it has white kernels and those inbreds have yellow kernels.

SYW-6R07086 has been observed as uniform and stable over two generations and it is within commercially acceptable limits. As is true with other sweet corn inbreds, a small percentage of variants can occur within commercially acceptable limits for almost any characteristic during the course of repeated multiplication. However, no known variants were observed during field trial observations or greenhouse crossing block observations.

B. PHYSIOLOGICAL AND MORPHOLOGICAL CHARACTERISTICS OF SWEET CORN LINE SYW-6R07086

In accordance with one aspect of the present invention, there is provided a plant having the physiological and morphological characteristics of sweet corn line SYW-6R07086. A description of the physiological and morphological characteristics of sweet corn line SYW-6R07086 is presented in Table 1.

TABLE 1

Physiological and Morphological Characteristics of Line SYW-6R07086

| Characteristic | SYW-6R07086 | Comparison Variety - WH98032 |
|---|---|---|
| 1. Type | sweet | sweet |
| 2. Region where developed in the U.S.A. | midwest | midwest |

TABLE 1-continued

Physiological and Morphological Characteristics of Line SYW-6R07086

| Characteristic | SYW-6R07086 | Comparison Variety - WH98032 |
|---|---|---|
| 3. Maturity in the Region of Best Adaptability | | |
| from emergence to 50% of plants in silk | days: 77<br>heat units: 1043.45 | days: 61<br>heat units: 1213.94 |
| from emergence to 50% of plants in pollen | days: 78<br>heat units: 1069.79 | days: 61<br>heat units: 1213.94 |
| from 10% to 90% pollen shed | days: 5<br>heat units: 109.95 | days: 5<br>heat units: 129.17 |
| from 50% silk to optimum edible quality | days: 20<br>heat units: 463.26 | days: 27<br>heat units: 544.01 |
| from 50% silk to harvest at 25% moisture | days: 58<br>heat units: 1286.16 | days: 72<br>heat units: 1194.35 |
| 4. Plant | | |
| length (tassel included) (inbred lines only) | short [W117] | medium |
| ratio height of insertion of upper ear to plant length | medium [F522] | small |
| plant height (to tassel tip) | 80.83 cm<br>standard deviation: 8.2325<br>sample size: 30 | 151.68 cm<br>standard deviation 16.6961<br>sample size: 60 |
| ear height (to base of top ear node) | 28.55 cm<br>standard deviation: 2.9456<br>sample size: 30 | 36.55 cm<br>standard deviation 4.691<br>sample size: 60 |
| length of top ear internode | 9.69 cm<br>standard deviation: 1.3924<br>sample size: 45 | 15.96 cm<br>standard deviation: 1.7137<br>sample size: 60 |
| average number of tillers | 2.35 avg<br>standard deviation: 0.8533<br>sample size: 45 | 2.23 avg<br>standard deviation 0.8823<br>sample size: 60 |
| average number of ears per stalk | 2.42 avg<br>standard deviation: 0.5469<br>sample size: 45 | 2.1 avg<br>standard deviation: 0.721<br>sample size: 60 |
| anthocyanin of brace roots | absent | absent |
| 5. Leaf | | |
| width of ear node leaf | 5.52 cm<br>standard deviation: 2.8369<br>sample size: 45 | 4.78 cm<br>standard deviation: 0.3651<br>sample size: 60 |
| length of ear node leaf in centimeters | 65.56 cm<br>standard deviation: 2.4063<br>sample size: 45 | 69.17 cm<br>standard deviation: 3.1451<br>sample size: 60 |
| number of leaves above top ear | 5.82<br>standard deviation: 0.7861<br>sample size: 45 | 5.49<br>standard deviation 0.5795<br>sample size: 60 |
| first leaf: anthocyanin coloration of sheath | absent or very weak | absent or very weak |
| first leaf: shape of tip | pointed to round | pointed to round |
| angle between blade and stem (on leaf just above upper ear) | very small | small |
| angle between blade and stem (on leaf just above upper ear) | slightly recurved [F1444] | very strongly recurved |
| degrees leaf angle | 56.86° | 67.49° |
| color | 5GY 3/4 | 5GY 4/4 |
| sheath pubescence (1 = none to 9 = like peach fuzz) | 7 | 6 |
| marginal waves (1 = none to 9 = many) | 3 | 8 |
| longitudinal creases (1 = none to 9 = many) | 8 | 3 |
| stem: degree of zig-zag | absent or very slight [Eva, Ivana] | slight |
| stem: anthocyanin coloration of brace roots | absent or very weak [W182E] | absent or very weak |
| leaf: width of blade (leaf of upper ear) | medium [A632] | medium |

TABLE 1-continued

Physiological and Morphological Characteristics of Line SYW-6R07086

| Characteristic | SYW-6R07086 | Comparison Variety - WH98032 |
|---|---|---|
| 6. Tassel | | |
| number of primary lateral branches | 31.12<br>standard deviation: 4.8422<br>sample size: 45 | 15.22<br>standard deviation: 3.8846<br>sample size: 60 |
| branch angle from central spike | 49.32°<br>standard deviation: 9.3681<br>sample size: 45 | 56.75°<br>standard deviation: 15.4995<br>sample size: 60 |
| length (from top leaf collar to tassel tip) | 27.32 cm<br>standard deviation: 2.1872<br>sample size: 45 | 36.29 cm<br>standard deviation: 2.9363<br>sample size: 60 |
| pollen shed (0 = male sterile to 9 = heavy shed) | 7 | 6 |
| anther color | 7.5GY 5/4 | 2.5GY 8/8 |
| glume color | 7.5GY 5/4 | 5GY 6/6 |
| bar glumes (glume bands) | absent | absent |
| time of anthesis (on middle third of main axis, 50% of plants) | medium to late [A632] | early to medium |
| anthocyanin coloration at base of glume (in middle third of main axis) | absent or very weak [W117] | absent or very weak |
| anthocyanin coloration of glumes excluding base (in middle third of main axis) | absent or very weak [F16] | weak |
| anthocyanin coloration of FRESH anthers (in middle third of main axis) | absent or very weak [F244] | absent or very weak |
| density of spikelets (in middle third of main axis) | medium [W401] | lax |
| angle between main axis and lateral branches (in lower third of tassel) | small [F257] | large |
| attitude of lateral branches (in lower third of tassel) | straight [F257] | recurved |
| number of primary lateral branches | many | few |
| ear: time of silk emergence (50% of plants) | late [M017] | medium to late |
| ear: anthocyanin coloration of silks | absent [F7] | absent |
| leaf: anthocyanin coloration of sheath (in middle of plant) | absent or very weak [F7] | absent or very weak |
| length of main axis above lowest side branch | short [EP1] | long |
| length of main axis above upper side branch | medium [F259] | long |
| length of side branches | medium [Rantzo] | long |
| 7. Ear | | |
| (unhusked data) silk color (3 days after emergence) | 2.5GY 8/4 | 2.5GY 8/6 |
| (unhusked data) fresh husk color (25 days after 50% silking) | 5GY 5/8 | 5GY 5/6 |
| (unhusked data) dry husk color (65 days after 50% silking) | 2.5Y 5/8 | 2.5Y 8/4 |
| (unhusked data) position of ear at dry husk stage | horizontal | upright |
| (unhusked data) husk tightness (1 = very loose to 9 = very tight) | 4 | 7 |
| (unhusked data) husk extension (at harvest) | long (8-10 cm beyond the ear tip) | short |
| (husked ear data) ear length | 13.57 cm<br>standard deviation: 1.3728<br>sample size: 45 | 15.49 cm<br>standard deviation: 1.323<br>sample size: 60 |

TABLE 1-continued

Physiological and Morphological Characteristics of Line SYW-6R07086

| Characteristic | SYW-6R07086 | Comparison Variety - WH98032 |
|---|---|---|
| (husked ear data) ear diameter at mid-point | 38.3 mm<br>standard deviation: 2.6625<br>sample size: 45 | 41.38 mm<br>standard deviation: 3.229<br>sample size: 60 |
| (husked ear data) ear weight | 43.2 gm<br>standard deviation: 12.5987<br>sample size: 45 | 68.24 gm<br>standard deviation: 13.7871<br>sample size: 60 |
| (husked ear data) number of kernel rows | 17.53<br>standard deviation: 2.2451<br>sample size: 45 | 18.93<br>standard deviation: 2.0532<br>sample size: 60 |
| (husked ear data) kernel rows | distinct | indistinct |
| (husked ear data) row alignment | spiral | straight |
| (husked ear data) shank length | 10.61 cm<br>standard deviation: 2.9578<br>sample size: 45 | 12.55 cm<br>standard deviation: 2.7562<br>sample size: 60 |
| (husked ear data) ear taper | average | slight |
| length of peduncle | medium [W182E] | medium |
| length (without husk) | medium [A654] | medium |
| diameter (in middle) | medium [W401] | medium |
| shape | conico-cylindrical [F7] | conico-cylindrical |
| number of rows of grain | medium [EP1] | medium |
| type of grain (in middle third of ear) | sweet [Jubilee] | sweet |
| color of top of grain | yellowish white | yellow |
| color of dorsal side of grain | yellowish white [A188] | yellow |
| anthocyanin coloration of glumes of cob | absent [F2] | absent |
| 8. Kernel (dried) | | |
| length | 9.85 mm<br>standard deviation: 1.5342<br>sample size: 45 | 9.91 mm<br>standard deviation: 1.0352<br>sample size: 60 |
| width | 6.19 mm<br>standard deviation: 1.2959<br>sample size: 45 | 6.05 mm<br>standard deviation: 0.9906<br>sample size: 60 |
| thickness | 3.16 mm<br>standard deviation: 1.1605<br>sample size: 45 | 3.03 mm<br>standard deviation 0.5761<br>sample size: 60 |
| % round kernels (shape grade) | 46.75%<br>sample size: 45 | 47.75%<br>sample size: 60 |
| aleurone color pattern | segregating | homozygous |
| aleurone color | 5Y 8/12 | 2.5Y 8/10 |
| hard endosperm color | 5Y 8/12 | 2.5Y 8/10 |
| endosperm type | sweet (su1) | sweet |
| weight per 100 kernels (unsized sample) | 6.2 gm<br>sample size: 200 | 9.38 gm<br>sample size: 200 |
| 9. Cob | | |
| diameter at mid-point | 23.65 mm<br>standard deviation: 1.4902<br>sample size: 30 | 27.88 mm<br>standard deviation: 1.4181<br>sample size: 60 |
| color | 5Y 8/4 | 5Y 8/4 |
| 10. Agronomic Traits | | |
| stay green (at 65 days after anthesis) (from 1 = worst to 9 = excellent) | 7 | 4 |

*These are typical values. Values may vary due to environment. Other values that are substantially equivalent are within the scope of the invention.

C. BREEDING SWEET CORN LINE SYW-6R07086

One aspect of the current invention concerns methods for crossing the sweet corn line SYW-6R07086 with itself or a second plant and the seeds and plants produced by such methods. These methods can be used for propagation of line SYW-6R07086, or can be used to produce hybrid corn seeds and the plants grown therefrom. Hybrid seeds are produced by crossing line SYW-6R07086 with second corn parent line.

The development of new varieties using one or more starting varieties is well known in the art. In accordance with the invention, novel varieties may be created by crossing line SYW-6R07086 followed by multiple generations of breeding according to such well known methods. New varieties may be created by crossing with any second plant. In selecting such a second plant to cross for the purpose of developing novel lines, it may be desired to choose those plants which either themselves exhibit one or more selected desirable characteristics or which exhibit the desired characteristic(s) when in hybrid combination. Once initial crosses have been made, inbreeding and selection take place to produce new varieties. For development of a uniform line, often five or more generations of selfing and selection are involved.

Uniform lines of new varieties may also be developed by way of double-haploids. This technique allows the creation of true breeding lines without the need for multiple generations of selfing and selection. In this manner true breeding lines can be produced in as little as one generation. Haploid embryos may be produced from microspores, pollen, anther cultures, or ovary cultures. The haploid embryos may then be doubled autonomously, or by chemical treatments (e.g. colchicine treatment). Alternatively, haploid embryos may be grown into haploid plants and treated to induce chromosome doubling. In either case, fertile homozygous plants are obtained. In accordance with the invention, any of such techniques may be used in connection with a plant of the invention and progeny thereof to achieve a homozygous line.

Backcrossing can also be used to improve an inbred plant. Backcrossing transfers a specific desirable trait from one inbred or non-inbred source to an inbred that lacks that trait. This can be accomplished, for example, by first crossing a superior inbred (A) (recurrent parent) to a donor inbred (non-recurrent parent), which carries the appropriate locus or loci for the trait in question. The progeny of this cross are then mated back to the superior recurrent parent (A) followed by selection in the resultant progeny for the desired trait to be transferred from the non-recurrent parent. After five or more backcross generations with selection for the desired trait, the progeny have the characteristic being transferred, but are like the superior parent for most or almost all other loci. The last backcross generation would be selfed to give pure breeding progeny for the trait being transferred.

The line of the present invention is particularly well suited for the development of new lines based on the elite nature of the genetic background of the line. In selecting a second plant to cross with SYW-6R07086 for the purpose of developing novel sweet corn lines, it will typically be preferred to choose those plants which either themselves exhibit one or more selected desirable characteristics or which exhibit the desired characteristic(s) when in hybrid combination. Examples of desirable traits may include, in specific embodiments, male sterility, herbicide resistance, resistance for bacterial, fungal, or viral disease, insect resistance, male fertility, sugar content, and enhanced nutritional quality.

D. FURTHER EMBODIMENTS OF THE INVENTION

In certain aspects, the invention provides plants modified to include at least a first desired heritable trait. Such plants may, in one embodiment, be developed by a plant breeding technique called backcrossing, wherein essentially all of the morphological and physiological characteristics of a variety are recovered in addition to a genetic locus transferred into the plant via the backcrossing technique. The term single locus converted plant as used herein refers to those corn plants which are developed by a plant breeding technique called backcrossing, wherein essentially all of the morphological and physiological characteristics of a variety are recovered in addition to the single locus transferred into the variety via the backcrossing technique. By essentially all of the morphological and physiological characteristics, it is meant that the characteristics of a plant are recovered that are otherwise present when compared in the same environment, other than an occasional variant trait that might arise during backcrossing or direct introduction of a transgene.

Backcrossing methods can be used with the present invention to improve or introduce a characteristic into the present variety. The parental corn plant which contributes the locus for the desired characteristic is termed the nonrecurrent or donor parent. This terminology refers to the fact that the nonrecurrent parent is used one time in the backcross protocol and therefore does not recur. The parental corn plant to which the locus or loci from the nonrecurrent parent are transferred is known as the recurrent parent as it is used for several rounds in the backcrossing protocol.

In a typical backcross protocol, the original variety of interest (recurrent parent) is crossed to a second variety (nonrecurrent parent) that carries the single locus of interest to be transferred. The resulting progeny from this cross are then crossed again to the recurrent parent and the process is repeated until a corn plant is obtained wherein essentially all of the morphological and physiological characteristics of the recurrent parent are recovered in the converted plant, in addition to the single transferred locus from the nonrecurrent parent.

The selection of a suitable recurrent parent is an important step for a successful backcrossing procedure. The goal of a backcross protocol is to alter or substitute a single trait or characteristic in the original variety. To accomplish this, a single locus of the recurrent variety is modified or substituted with the desired locus from the nonrecurrent parent, while retaining essentially all of the rest of the desired genetic, and therefore the desired physiological and morphological constitution of the original variety. The choice of the particular nonrecurrent parent will depend on the purpose of the backcross; one of the major purposes is to add some commercially desirable trait to the plant. The exact backcrossing protocol will depend on the characteristic or trait being altered and the genetic distance between the recurrent and nonrecurrent parents. Although backcrossing methods are simplified when the characteristic being transferred is a dominant allele, a recessive allele, or an additive allele (between recessive and dominant), may also be transferred. In this instance it may be necessary to introduce a test of the progeny to determine if the desired characteristic has been successfully transferred.

In one embodiment, progeny corn plants of a backcross in which SYW-6R07086 is the recurrent parent comprise (i) the desired trait from the non-recurrent parent and (ii) all of the physiological and morphological characteristics of sweet corn line SYW-6R07086 as determined at the 5% significance level when grown in the same environmental conditions.

New varieties can also be developed from more than two parents. The technique, known as modified backcrossing, uses different recurrent parents during the backcrossing. Modified backcrossing may be used to replace the original recurrent parent with a variety having certain more desirable characteristics or multiple parents may be used to obtain different desirable characteristics from each.

With the development of molecular markers associated with particular traits, it is possible to add additional traits into an established germ line, such as represented here, with the end result being substantially the same base germplasm with the addition of a new trait or traits. Molecular breeding, as described in Moose and Mumm, 2008 (Plant Physiology, 147: 969-977), for example, and elsewhere, provides a mechanism for integrating single or multiple traits or QTL into an elite line. This molecular breeding-facilitated movement of a trait or traits into an elite line may encompass incorporation of a particular genomic fragment associated with a particular trait of interest into the elite line by the mechanism of identification of the integrated genomic fragment with the use of flanking or associated marker assays. In the embodiment represented here, one, two, three or four genomic loci, for example, may be integrated into an elite line via this methodology. When this elite line containing the additional loci is further crossed with another parental elite line to produce hybrid offspring, it is possible to then incorporate at least eight separate additional loci into the hybrid. These additional loci may confer, for example, such traits as a disease resistance or a fruit quality trait. In one embodiment, each locus may confer a separate trait. In another embodiment, loci may need to be homozygous and exist in each parent line to confer a trait in the hybrid. In yet another embodiment, multiple loci may be combined to confer a single robust phenotype of a desired trait.

Many single locus traits have been identified that are not regularly selected for in the development of a new inbred but that can be improved by backcrossing techniques. Single locus traits may or may not be transgenic; examples of these traits include, but are not limited to, male sterility, waxy starch, herbicide resistance, resistance to bacterial, fungal, or viral disease, insect resistance, sugar content, male fertility and enhanced nutritional quality. These genes are generally inherited through the nucleus, but may be inherited through the cytoplasm. Some known exceptions to this are genes for male sterility, some of which are inherited cytoplasmically, but still act as a single locus trait.

Direct selection may be applied where the single locus acts as a dominant trait. For this selection process, the progeny of the initial cross are assayed for viral resistance and/or the presence of the corresponding gene prior to the backcrossing. Selection eliminates any plants that do not have the desired gene and resistance trait, and only those plants that have the trait are used in the subsequent backcross. This process is then repeated for all additional backcross generations.

Selection of corn plants for breeding is not necessarily dependent on the phenotype of a plant and instead can be based on genetic investigations. For example, one can utilize a suitable genetic marker which is closely genetically linked to a trait of interest. One of these markers can be used to identify the presence or absence of a trait in the offspring of a particular cross, and can be used in selection of progeny for continued breeding. This technique is commonly referred to as marker assisted selection. Any other type of genetic marker or other assay which is able to identify the relative presence or absence of a trait of interest in a plant can also be useful for breeding purposes. Procedures for marker assisted selection are well known in the art. Such methods will be of particular utility in the case of recessive traits and variable phenotypes, or where conventional assays may be more expensive, time consuming or otherwise disadvantageous. Types of genetic markers which could be used in accordance with the invention include, but are not necessarily limited to, Simple Sequence Length Polymorphisms (SSLPs) (Williams et al., *Nucleic Acids Res.,* 1 8:6531 6535, 1990), Randomly Amplified Polymorphic DNAs (RAPDs), DNA Amplification Fingerprinting (DAF), Sequence Characterized Amplified Regions (SCARs), Arbitrary Primed Polymerase Chain Reaction (AP-PCR), Amplified Fragment Length Polymorphisms (AFLPs) (EP 534 858, specifically incorporated herein by reference in its entirety), and Single Nucleotide Polymorphisms (SNPs) (Wang et al., *Science,* 280:1077-1082, 1998).

E. PLANTS DERIVED BY GENETIC ENGINEERING

Many useful traits that can be introduced by backcrossing, as well as directly into a plant, are those which are introduced by genetic transformation techniques. Genetic transformation may therefore be used to insert a selected transgene into the sweet corn line of the invention or may, alternatively, be used for the preparation of transgenes which can be introduced by backcrossing. Methods for the transformation of plants that are well known to those of skill in the art and applicable to many crop species include, but are not limited to, electroporation, microprojectile bombardment, *Agrobacterium*-mediated transformation and direct DNA uptake by protoplasts.

To effect transformation by electroporation, one may employ either friable tissues, such as a suspension culture of cells or embryogenic callus or alternatively one may transform immature embryos or other organized tissue directly. In this technique, one would partially degrade the cell walls of the chosen cells by exposing them to pectin-degrading enzymes (pectolyases) or mechanically wound tissues in a controlled manner.

An efficient method for delivering transforming DNA segments to plant cells is microprojectile bombardment. In this method, particles are coated with nucleic acids and delivered into cells by a propelling force. Exemplary particles include those comprised of tungsten, platinum, and preferably, gold. For the bombardment, cells in suspension are concentrated on filters or solid culture medium. Alternatively, immature embryos or other target cells may be arranged on solid culture medium. The cells to be bombarded are positioned at an appropriate distance below the macroprojectile stopping plate.

Microprojectile bombardment techniques are widely applicable, and may be used to transform virtually any plant species. An illustrative embodiment of a method for delivering DNA into plant cells by acceleration is the Biolistics Particle Delivery System, which can be used to propel particles coated with DNA or cells through a screen, such as a stainless steel or Nytex screen, onto a surface covered with target cells. The screen disperses the particles so that they are not delivered to the recipient cells in large aggregates.

*Agrobacterium*-mediated transfer is another widely applicable system for introducing gene loci into plant cells. An advantage of the technique is that DNA can be introduced into whole plant tissues, thereby bypassing the need for regeneration of an intact plant from a protoplast. Modern *Agrobacterium* transformation vectors are capable of replication in *E. coli* as well as *Agrobacterium*, allowing for convenient manipulations (Klee et al., *Bio-Technology,* 3(7):637-642, 1985). Moreover, recent technological advances in vectors for *Agrobacterium*-mediated gene transfer have improved the arrangement of genes and restriction sites in the vectors to facilitate the construction of vectors capable of expressing various polypeptide coding genes. The vectors described have convenient multi-linker regions flanked by a promoter and a polyadenylation site for direct expression of inserted polypeptide coding genes. Additionally, *Agrobacterium* containing both armed and disarmed Ti genes can be used for transformation.

In those plant strains where *Agrobacterium*-mediated transformation is efficient, it is the method of choice because of the facile and defined nature of the gene locus transfer. The use of *Agrobacterium*-mediated plant integrating vectors to introduce DNA into plant cells is well known in the art (Fraley et al., *Bio/Technology*, 3:629-635, 1985; U.S. Pat. No. 5,563,055).

Transformation of plant protoplasts also can be achieved using methods based on calcium phosphate precipitation, polyethylene glycol treatment, electroporation, and combinations of these treatments (see, e.g., Potrykus et al., *Mol. Gen. Genet.*, 199:183-188, 1985; Omirulleh et al., *Plant Mol. Biol.*, 21(3):415-428, 1993; Fromm et al., *Nature*, 312:791-793, 1986; Uchimiya et al., *Mol. Gen. Genet.*, 204:204, 1986; Marcotte et al., *Nature*, 335:454, 1988). Transformation of plants and expression of foreign genetic elements is exemplified in Choi et al. (*Plant Cell Rep.*, 13: 344-348, 1994), and Ellul et al. (*Theor. Appl. Genet.*, 107:462-469, 2003).

A number of promoters have utility for plant gene expression for any gene of interest including but not limited to selectable markers, scoreable markers, genes for pest tolerance, disease resistance, nutritional enhancements and any other gene of agronomic interest. Examples of constitutive promoters useful for plant gene expression include, but are not limited to, the cauliflower mosaic virus (CaMV) P-35S promoter, which confers constitutive, high-level expression in most plant tissues (see, e.g., Odel et al., *Nature*, 313:810, 1985), including in monocots (see, e.g., Dekeyser et al., *Plant Cell*, 2:591, 1990; Terada and Shimamoto, *Mol. Gen. Genet.*, 220:389, 1990); a tandemly duplicated version of the CaMV 35S promoter, the enhanced 35S promoter (P-e35S) the nopaline synthase promoter (An et al., *Plant Physiol.*, 88:547, 1988), the octopine synthase promoter (Fromm et al., *Plant Cell*, 1:977, 1989); and the figwort mosaic virus (P-FMV) promoter as described in U.S. Pat. No. 5,378,619 and an enhanced version of the FMV promoter (P-eFMV) where the promoter sequence of P-FMV is duplicated in tandem, the cauliflower mosaic virus 19S promoter, a sugarcane bacilliform virus promoter, a commelina yellow mottle virus promoter, and other plant DNA virus promoters known to express in plant cells.

A variety of plant gene promoters that are regulated in response to environmental, hormonal, chemical, and/or developmental signals can also be used for expression of an operably linked gene in plant cells, including promoters regulated by (1) heat (Callis et al., *Plant Physiol.*, 88:965, 1988), (2) light (e.g., pea rbcS-3A promoter, Kuhlemeier et al., *Plant Cell*, 1:471, 1989; maize rbcS promoter, Schaffner and Sheen, *Plant Cell*, 3:997, 1991; or chlorophyll a/b-binding protein promoter, Simpson et al., *EMBO J.*, 4:2723, 1985), (3) hormones, such as abscisic acid (Marcotte et al., *Plant Cell*, 1:969, 1989), (4) wounding (e.g., wun1, Siebertz et al., *Plant Cell*, 1:961, 1989); or (5) chemicals such as methyl jasmonate, salicylic acid, or Safener. It may also be advantageous to employ organ-specific promoters (e.g., Roshal et al., *EMBO J.*, 6:1155, 1987; Schernthaner et al., *EMBO J.*, 7:1249, 1988; Bustos et al., *Plant Cell*, 1:839, 1989).

Exemplary nucleic acids which may be introduced to plants of this invention include, for example, DNA sequences or genes from another species, or even genes or sequences which originate with or are present in the same species, but are incorporated into recipient cells by genetic engineering methods rather than classical reproduction or breeding techniques. However, the term "exogenous" is also intended to refer to genes that are not normally present in the cell being transformed, or perhaps simply not present in the form, structure, etc., as found in the transforming DNA segment or gene, or genes which are normally present and that one desires to express in a manner that differs from the natural expression pattern, e.g., to over-express. Thus, the term "exogenous" gene or DNA is intended to refer to any gene or DNA segment that is introduced into a recipient cell, regardless of whether a similar gene may already be present in such a cell. The type of DNA included in the exogenous DNA can include DNA which is already present in the plant cell, DNA from another plant, DNA from a different organism, or a DNA generated externally, such as a DNA sequence containing an antisense message of a gene, or a DNA sequence encoding a synthetic or modified version of a gene.

Many hundreds if not thousands of different genes are known and could potentially be introduced into a corn plant according to the invention. Non-limiting examples of particular genes and corresponding phenotypes one may choose to introduce into a corn plant include one or more genes for insect tolerance, such as a *Bacillus thuringiensis* (B.t.) gene, pest tolerance such as genes for fungal disease control, herbicide tolerance such as genes conferring glyphosate tolerance, and genes for quality improvements such as yield, nutritional enhancements, environmental or stress tolerances, or any desirable changes in plant physiology, growth, development, morphology or plant product(s). For example, structural genes would include any gene that confers insect tolerance including but not limited to a *Bacillus* insect control protein gene as described in WO 99/31248, herein incorporated by reference in its entirety, U.S. Pat. No. 5,689,052, herein incorporated by reference in its entirety, U.S. Pat. Nos. 5,500,365 and 5,880,275, herein incorporated by reference in their entirety. In another embodiment, the structural gene can confer tolerance to the herbicide glyphosate as conferred by genes including, but not limited to *Agrobacterium* strain CP4 glyphosate resistant EPSPS gene (aroA:CP4) as described in U.S. Pat. No. 5,633,435, herein incorporated by reference in its entirety, or glyphosate oxidoreductase gene (GOX) as described in U.S. Pat. No. 5,463,175, herein incorporated by reference in its entirety.

Alternatively, the DNA coding sequences can affect these phenotypes by encoding a non-translatable RNA molecule that causes the targeted inhibition of expression of an endogenous gene, for example via antisense- or cosuppression-mediated mechanisms (see, for example, Bird et al., *Biotech. Gen. Engin. Rev.*, 9:207, 1991). The RNA could also be a catalytic RNA molecule (i.e., a ribozyme) engineered to cleave a desired endogenous mRNA product (see for example, Gibson and Shillito, *Mol. Biotech.*, 7:125, 1997). Thus, any gene which produces a protein or mRNA which expresses a phenotype or morphology change of interest is useful for the practice of the present invention.

F. DEFINITIONS

In the description and tables herein, a number of terms are used. In order to provide a clear and consistent understanding of the specification and claims, the following definitions are provided:

Allele: Any of one or more alternative forms of a gene locus, all of which alleles relate to one trait or characteristic. In a diploid cell or organism, the two alleles of a given gene occupy corresponding loci on a pair of homologous chromosomes.

Backcrossing: A process in which a breeder repeatedly crosses hybrid progeny, for example a first generation hybrid ($F_1$), back to one of the parents of the hybrid progeny. Backcrossing can be used to introduce one or more single locus conversions from one genetic background into another.

Crossing: The mating of two parent plants.

Cross-pollination: Fertilization by the union of two gametes from different plants.

Diploid: A cell or organism having two sets of chromosomes.

Emasculate: The removal of plant male sex organs or the inactivation of the organs with a cytoplasmic or nuclear genetic factor or a chemical agent conferring male sterility.

Enzymes: Molecules which can act as catalysts in biological reactions.

$F_1$ Hybrid: The first generation progeny of the cross of two nonisogenic plants.

Genotype: The genetic constitution of a cell or organism.

Haploid: A cell or organism having one set of the two sets of chromosomes in a diploid.

Linkage: A phenomenon wherein alleles on the same chromosome tend to segregate together more often than expected by chance if their transmission was independent.

Marker: A readily detectable phenotype, preferably inherited in codominant fashion (both alleles at a locus in a diploid heterozygote are readily detectable), with no environmental variance component, i.e., heritability of 1.

Phenotype: The detectable characteristics of a cell or organism, which characteristics are the manifestation of gene expression.

Quantitative Trait Loci (QTL): Quantitative trait loci (QTL) refer to genetic loci that control to some degree numerically representable traits that are usually continuously distributed.

Resistance: As used herein, the terms "resistance" and "tolerance" are used interchangeably to describe plants that show no symptoms to a specified biotic pest, pathogen, abiotic influence or environmental condition. These terms are also used to describe plants showing some symptoms but that are still able to produce marketable product with an acceptable yield. Some plants that are referred to as resistant or tolerant are only so in the sense that they may still produce a crop, even though the plants are stunted and the yield is reduced.

Regeneration: The development of a plant from tissue culture.

Self-pollination: The transfer of pollen from the anther to the stigma of the same plant.

Single Locus Converted (Conversion) Plant: Plants which are developed by a plant breeding technique called backcrossing, wherein essentially all of the morphological and physiological characteristics of a corn variety are recovered in addition to the characteristics of the single locus transferred into the variety via the backcrossing technique and/or by genetic transformation.

Substantially Equivalent: A characteristic that, when compared, does not show a statistically significant difference (e.g., $p=0.05$) from the mean.

Tissue Culture: A composition comprising isolated cells of the same or a different type or a collection of such cells organized into parts of a plant.

Transgene: A genetic locus comprising a sequence which has been introduced into the genome of a corn plant by transformation.

G. DEPOSIT INFORMATION

A deposit of sweet corn line SYW-6R07086, disclosed above and recited in the claims, has been made with the American Type Culture Collection (ATCC), 10801 University Blvd., Manassas, Va. 20110-2209. The date of deposit was Dec. 6, 2011. The accession number for those deposited seeds of sweet corn line SYW-6R07086 is ATCC Accession No. PTA-12306. Upon issuance of a patent, all restrictions upon the deposit will be removed, and the deposit is intended to meet all of the requirements of 37 C.F.R. §1.801-1.809. The deposit will be maintained in the depository for a period of 30 years, or 5 years after the last request, or for the effective life of the patent, whichever is longer, and will be replaced if necessary during that period.

Although the foregoing invention has been described in some detail by way of illustration and example for purposes of clarity and understanding, it will be obvious that certain changes and modifications may be practiced within the scope of the invention, as limited only by the scope of the appended claims.

All references cited herein are hereby expressly incorporated herein by reference.

What is claimed is:

1. A seed of sweet corn line SYW-6R07086, a sample of seed of said line having been deposited under ATCC Accession Number PTA-12306.

2. A plant of sweet corn line SYW-6R07086, a sample of seed of said line having been deposited under ATCC Accession Number PTA-12306.

3. A plant part of the plant of claim 2.

4. The plant part of claim 3, wherein said part is selected from the group consisting of an ear, ovule, pollen or cell.

5. A sweet corn plant, or a part thereof, having all the physiological and morphological characteristics of the sweet corn plant of claim 2.

6. A tissue culture of regenerable cells of sweet corn line SYW-6R07086, a sample of seed of said line having been deposited under ATCC Accession Number PTA-12306.

7. The tissue culture according to claim 6, comprising cells or protoplasts from a plant part selected from the group consisting of leaf, pollen, embryo, root, root tip, anther, silk, tassel, kernel, ear, cob, husk, stalk and meristem.

8. A sweet corn plant regenerated from the tissue culture of claim 6, wherein the regenerated plant expresses all of the physiological and morphological characteristics of sweet corn line SYW-6R07086, a sample of seed of said line having been deposited under ATCC Accession Number PTA-12306.

9. A method of producing seed, comprising crossing the plant of claim 2 with itself or a second plant.

10. The method of claim 9, wherein the plant of sweet corn line SYW-6R07086 is the female parent.

11. The method of claim 9, wherein the plant of sweet corn line SYW-6R07086 is the male parent.

12. An F1 hybrid seed produced by the method of claim 9.

13. An F1 hybrid plant produced by growing the seed of claim 12.

14. A plant produced by introducing a single locus conversion into sweet corn line SYW-6R07086, or a selfed progeny thereof, wherein the single locus was introduced into sweet corn line SYW-6R07086 by backcrossing or genetic transformation and wherein a sample of seed of sweet corn line SYW-6R07086 has been deposited under ATCC Accession Number PTA-12306, wherein the plant otherwise comprises essentially all of the morphological and physiological characteristics of sweet corn line SYW-6R07086.

15. The plant of claim 14, wherein the single locus conversion comprises a transgene.

16. A seed that produces the plant of claim 14.

17. The seed of claim 16, wherein the single locus confers a trait selected from the group consisting of male sterility, herbicide tolerance, insect or pest resistance, disease resistance, modified fatty acid metabolism, abiotic stress resistance, altered seed amino acid composition, site-specific genetic recombination, and modified carbohydrate metabolism.

18. The seed of claim 17, wherein the herbicide tolerance trait is tolerance to an herbicide selected from the group consisting of glyphosate, sulfonylurea, imidazalinone, dicamba, glufosinate, phenoxy proprionic acid, cycloshexone, triazine, benzonitrile, PPO-inhibitor herbicides and broxynil.

19. A method of producing a seed of a progeny plant derived from the sweet corn line SYW-6R07086, the method comprising crossing a plant of sweet corn line SYW-6R07086 with a corn plant of a second line to produce at least a first seed, wherein a sample of seed of sweet corn line SYW-6R07086 has been deposited under ATCC Accession Number PTA-12306.

20. The method of claim 19, further comprising the steps of
   (a) crossing a plant grown from said seed with itself or a second plant to produce a seed of a progeny plant of a subsequent generation;
   (b) growing a progeny plant of a subsequent generation from said seed and crossing the progeny plant of a subsequent generation with itself or a second plant; and
   (c) repeating steps (a) and (b) with sufficient inbreeding until a seed of an inbred corn plant derived from the sweet corn line SYW-6R07086 is produced.

21. The method of claim 20, further comprising crossing said inbred corn plant derived from sweet corn line SYW-6R07086 with a corn plant of a different genotype to produce seed of a hybrid plant derived from sweet corn line SYW-6R07086.

22. A method of producing food or feed comprising obtaining the plant of claim 2 or a part thereof and producing said food or feed therefrom.

* * * * *